(12) United States Patent
Li et al.

(10) Patent No.: US 9,767,620 B2
(45) Date of Patent: Sep. 19, 2017

(54) GESTURE-BASED EDITING OF 3D MODELS FOR HAIR TRANSPLANTATION APPLICATIONS

(71) Applicant: Restoration Robotics, Inc., San Jose, CA (US)

(72) Inventors: Steven X Li, Sunnyvale, CA (US); Hui Zhang, San Jose, CA (US); Ognjen Petrovic, Mountain View, CA (US); Gabriele Zingaretti, Capitola, CA (US)

(73) Assignee: RESTORATION ROBOTICS, INC., San Jose, CA (US)

( * ) Notice: Subject to any disclaimer, the term of this patent is extended or adjusted under 35 U.S.C. 154(b) by 282 days.

(21) Appl. No.: 14/555,291

(22) Filed: Nov. 26, 2014

(65) Prior Publication Data
US 2016/0148435 A1 May 26, 2016

(51) Int. Cl.
| G06T 19/20 | (2011.01) |
| G06F 3/0484 | (2013.01) |
| G06F 3/0481 | (2013.01) |
| G06F 3/0482 | (2013.01) |
| G06F 3/0488 | (2013.01) |
| A61B 34/10 | (2016.01) |

(52) U.S. Cl.
CPC .............. *G06T 19/20* (2013.01); *A61B 34/10* (2016.02); *G06F 3/0482* (2013.01); *G06F 3/04817* (2013.01); *G06F 3/04842* (2013.01); *G06F 3/04845* (2013.01); *G06F 3/04883* (2013.01); *G06T 2200/24* (2013.01); *G06T 2210/41* (2013.01)

(58) Field of Classification Search
CPC ........ G06T 19/20; G06T 11/203; G06T 17/00
See application file for complete search history.

(56) References Cited

U.S. PATENT DOCUMENTS

| 5,680,523 A | 10/1997 | Watkins et al. |
| 6,125,197 A | 9/2000 | Mackq et al. |
| 6,233,351 B1 * | 5/2001 | Feeney .............. G06K 9/00416 345/522 |

(Continued)

FOREIGN PATENT DOCUMENTS

| EP | 1510973 | 3/2005 |
| WO | 96/14622 | 5/1996 |

(Continued)

OTHER PUBLICATIONS

Balan, "Voxel Carving and Coloring—Contructing a 3D Model of an Object from 2D Images", Computer Science Department. Brown University, 7 pages.

(Continued)

*Primary Examiner* — Gregory J Tryder
*Assistant Examiner* — Diane Wills (57) ABSTRACT

Methods and systems are provided for gesture-based editing of three-dimensional (3D) models of real targets, for example, for use in planning hair transplantation procedures. According to some embodiments of the methodology disclosed, a 3D control points on an initial default model are matched automatically with the drawing of an outline of a target feature that a user wishes to define and deformed appropriately to quickly and accurately modify and update the initial default model into a resulting fitting model of the real target.

29 Claims, 5 Drawing Sheets

(56) References Cited

U.S. PATENT DOCUMENTS

| | | | |
|---|---|---|---|
| 6,585,746 | B2 | 7/2003 | Gildenberg |
| 6,879,946 | B2 | 4/2005 | Rong et al. |
| 7,212,664 | B2 | 5/2007 | Lee et al. |
| 7,806,121 | B2 | 10/2010 | Bodduluri |
| 7,835,568 | B2 | 11/2010 | Park et al. |
| 7,856,125 | B2 | 12/2010 | Medioni et al. |
| 8,699,787 | B2 | 4/2014 | Van Den Hengel et al. |
| 2002/0041285 | A1 | 4/2002 | Hunter et al. |
| 2002/0095276 | A1 | 7/2002 | Rong et al. |
| 2005/0031194 | A1 | 2/2005 | Lee et al. |
| 2005/0063582 | A1* | 3/2005 | Park .................. G06T 17/10 382/154 |
| 2005/0162419 | A1 | 7/2005 | Kim et al. |
| 2007/0106306 | A1* | 5/2007 | Bodduluri ........ A61B 17/32053 606/133 |
| 2007/0183653 | A1* | 8/2007 | Medioni ............ G06K 9/00208 382/154 |
| 2009/0322860 | A1 | 12/2009 | Zhang et al. |
| 2010/0092072 | A1 | 4/2010 | Guntur |
| 2011/0107270 | A1 | 5/2011 | Wang et al. |
| 2012/0183238 | A1 | 7/2012 | Savvides et al. |
| 2013/0129141 | A1* | 5/2013 | Wang .................. G06K 9/00 382/103 |
| 2013/0181986 | A1* | 7/2013 | Fowler ................ G06T 17/30 345/420 |
| 2013/0287294 | A1 | 10/2013 | Ye et al. |
| 2014/0043329 | A1* | 2/2014 | Wang .................. G06T 17/20 345/420 |
| 2014/0163931 | A1 | 6/2014 | Snyder et al. |
| 2014/0261467 | A1 | 9/2014 | Zhang et al. |
| 2014/0278321 | A1 | 9/2014 | Zhang et al. |
| 2015/0097829 | A1* | 4/2015 | Algreatly ............ G06T 13/20 345/420 |
| 2015/0278590 | A1* | 10/2015 | Gunjan ............ G06K 9/00362 382/107 |

FOREIGN PATENT DOCUMENTS

| | | |
|---|---|---|
| WO | 03/081536 | 10/2003 |
| WO | 2004/047008 | 6/2004 |
| WO | 2006/056614 | 6/2006 |
| WO | 2012/126135 | 9/2012 |
| WO | 2013/024418 | 2/2013 |

OTHER PUBLICATIONS

Elias, "3D Model Reconstruction From Vector Perpendicular Projections", Scientific Monographs in Automation and Computer Science. vol. 1. Ilmenau Technical Library, 2012.

Faggian, et al., "3D Morphable Model Fitting from Multiple Views", IEEE, 2008, 6 pages.

Park, et al., "3D Face Reconstruction from Stereo Video", First International Workshop on Video Processing for Security (VP4S-06), Jun. 7-9, Quebec City, Canada, 2006.

Payet, et al., "From Contours to 3D Object Detection and Pose Estimation", Proc. 13th International Conference on Computer Vision (ICCV) 2011, 2011, 1-9.

Qin, et al., "Extracting 2D Projection Contour from 3D Model Using Ring-Relationship-Based Method", Information Technology Journal 6(6), 2007, 914-918.

Zhu, et al., "Construction of 3D Human Distal Femoral Surface Models Using a 3D Statistical Deformable Model", J Biomech. Sep. 2, 2011; 44(13), Sep. 2, 2011, 2362-2368.

\* cited by examiner

GESTURE-BASED EDITING OF 3D MODELS FOR HAIR TRANSPLANTATION APPLICATIONS

FIELD OF THE INVENTION

The present disclosure generally relates to gesture-based editing of three-dimensional (3D) models of real targets, and more particularly to methods and systems used for editing 3D models using gesture generated traces, in particular for, but not limited to, medical/cosmetic applications, such as for use in the planning of hair transplantation procedures wherein real targets are patients' heads.

In the following of the present specification, reference will be mainly made to editing of 3D models of patients' heads in reference to the planning of medical/cosmetic applications. However, it must be understood that the gesture-based editing of 3D models according to the present disclosure may be also used for editing models of different parts of a person's body or even objects and/or in different applications availing of computer graphics, e.g. for processing and showing the appearance of a person or of an arrangement such as in virtual simulations of a person's appearance when a tattoo is applied, when wearing glasses or hats (in which case the real target may include both at least one part of a person's body and at least one object) or of a vehicle when provided with optional additional equipment (in which case the real target may include more than one object), still remaining within the scope of protection of the present disclosure.

BACKGROUND

It is useful to easily and accurately edit 3D models of patients, for example, in the cosmetic surgery field. An accurate 3D model does not only speed up the overall surgery workflow but also improves patient confidence on a positive outcome of the procedure.

Currently available modeling techniques, which sometimes preliminarily require acquiring statistical data of a population of real targets, are based on complex 3D modeling applications. Other modeling techniques are based on adding and subtracting geometric primitives (Constructive Solid Geometry), and they are widely used in CAD and gaming applications. Examples of these modeling techniques comprise those used in Maya® 3D animation, available from Autodesk Inc., and Rhinoceros® 3D, available from Robert McNeel & Associates, that support the non-uniform rational basis-splines (NURBS) mathematical model. Further modeling techniques based on complex methods are disclosed in U.S. Pat. No. 5,680,523 and in US patent applications published as Nos. 2002/0095276 A1, 2005/0031194 A1, 2005/0063582 A1 and 2005/162419 A1.

Due to their complexity, currently available modeling techniques result in procedures which are time-consuming and very cumbersome for the user, e.g. a physician operator. For instance, with reference to 3D head models of patients for the planning of medical/cosmetic applications, 3D modeling applications usually preliminary require users to edit feature reference points on patient's bi-dimensional (2D) photographs (shown on a display) one by one, which feature reference points in turn deform a default 3D head model, and after editing such feature reference points, a user may still need to edit individual model control points one by one to create an accurate representation of the patient's facial/cranial features.

SUMMARY

In view of the above, it is an object of this disclosure to allow in a simple, reliable, effective, fast and comfortable way to obtain a 3D model of a target, such as a part of a person's body, in particular a head, or even an object.

In accordance with one general aspect, methods and systems are disclosed for gesture-based editing of three-dimensional (3D) models of real targets that are more intuitive than currently available modeling techniques. The methodology of the present disclosure allows the user to easily draw an outline of the target feature he or she wishes to define for the 3D model to edit—for instance, when the target is a head, any contour profile of chin, jaw, upper or lower lip, mouth, right or left ear, brow (i.e. supraorbital) ridge, front hairline or top head —, and 3D control points on an initial default model are matched automatically with the drawn outline(s) and deformed appropriately to quickly and accurately modify and update the initial default model into a resulting fitting model of the real target.

One embodiment of the method comprises the following steps:

selecting a 2D projected view of a 3D default model, wherein the 3D default model comprises an overall set of vertices, wherein a plurality of subsets of the overall set of vertices forms a plurality of 3D feature groups, each 3D feature group comprises an ordered set of feature group points that are associated with a respective specific feature of the default model;

selecting a 2D image of the real target which corresponds to the selected 2D projected view of the default model, and displaying the selected 2D image of the real target on a display;

acquiring at least one line traced by a user over the display that follows at least one specific feature of the real target visible in the 2D image which correspond to at least one specific feature group;

identifying an ordered set of user points belonging to the at least one traced line;

matching the user points against the feature group points of the at least one specific feature group in a transformed 2D space of first transformed coordinate L and second transformed coordinate Th, where the first transformed coordinate L of a point is a normalized length in a Cartesian coordinate system of the point in its ordered set of points joined by segments, and the second transformed coordinate Th of the point is an angle of discrete vector difference in the Cartesian coordinate system between two discrete successive vectors respectively following and preceding the point in its ordered set, wherein a subset of user points are identified as best matches of the feature group points of the at least one specific feature group; and updating the 3D default model by applying to the feature group points of the at least one specific feature group 3D geometric difference vectors calculated for each pair of a feature group point and a respective user point identified as best match of such feature group point.

According to another aspect, the method may further comprise smoothing the 3D model for obtaining a fitting model of the real target.

According to yet another aspect, matching can be based on a least distance criterion in the transformed 2D space.

According to further aspect, matching may comprise: calculating first transformed coordinate L for each feature Group Point of the at least one specific feature group and for each user point, for each feature group point of the at least one specific feature group, identifying the user point having first transformed coordinate L closest to the first transformed coordinate L of the Feature group point under consideration, whereby a subset of user points are selected to be provisionally anchored to the feature group points of the at least one specific feature group, using each point of the subset of user points as starting points for a recursive best match search for each feature group point of the at least one specific feature group, wherein the recursive best match search searches for a user point of the ordered set of user points belonging to the at least one traced line having the least distance from the feature group point in the transformed 2D space of first transformed coordinate L and second transformed coordinate Th, whereby for each feature group point of the at least one specific feature group a user point of the ordered set of user points belonging to the at least one traced line is identified as best match of the feature group point.

According to yet another aspect, for each feature group point of the at least one specific feature group the recursive best match search may comprise:

assuming the provisionally anchored user point as guess best match of the feature group point, selecting a tuple of successive points of the ordered set of user points belonging to the at least one traced line including the guess best match, comparing distances in the transformed 2D space of first transformed coordinate L and second transformed coordinate Th of the successive points of the tuple from the feature group point, whereby a provisional least distant point having the least distance from the feature group point is identified, and stopping recursion when the provisional least distant point is the best guess match.

According to a further aspect, if the provisional least distant point is not the best match, the recursive best match search may comprise assuming the provisional least distant point as best guess match of the feature group point and making another recursion of selecting a tuple of successive points of the ordered set of user points and comparing distances of the successive points of the tuple from the feature group point.

According to a further aspect, a tuple of successive points of the ordered set of user points may include three or more points.

According to another aspect, a tuple of successive points of the ordered set of user points may include an odd number of points, wherein the guess best match is a central point of the tuple.

According to an additional aspect, a ratio of total number of user points to total number of feature group points of the at least one specific feature group may range from 20 to 5000.

According to a yet another aspect, the 2D projected view may be selected from the group comprising five orthogonal 2D projected views including a front view, a back view, a left view, a right view, and a top view.

According to a further aspect, the 2D projected view may be selected from the group comprising six orthogonal 2D projected views including a front view, a back view, a left view, a right view, a top view and a bottom view.

According to an additional aspect, the user may trace the at least one line by interacting with at least one pointing device.

According to another aspect, the at least one pointing device may include any appropriate pointing device, for example, a mouse and/or a touch-screen display.

According to a further aspect, acquiring the at least one line traced by a user over the display may include receiving an indication of the at least one specific feature group of the default model to which the at least one traced line corresponds, wherein receiving an indication may optionally include selecting the at least one specific feature group of the default model from a list of icons displayed in a menu on the display.

According to an additional aspect, smoothing may be based on one or more techniques selected from the group comprising cubic splines, Bezier curves and Gaussian kernel convolution.

According to a yet another aspect, smoothing may include applying any local distortion from the default model to the fitting model to a texture map grabbed from the 2D image of the real target.

According to a further aspect, the method may further comprise, after smoothing, checking a feedback from the user for allowing the user to reject the modified model (e.g., delete any change of the default model or go back and start again from the default model), or to further modify the just obtained fitting model by setting the just obtained fitting model as default model and by repeating any or all of the steps of the method to further modify it.

According to yet another aspect, the method may further comprise allowing the user to combine the method with one or more other 3D model editing techniques.

According to an additional aspect, the real target can be at least one part of a person's body and/or at least one object.

According to another aspect, the real target may be a person's head, and the plurality of 3D feature groups can optionally include one or more of the feature groups selected from the group comprising a jaw line feature group, a laryngeal prominence feature group, an upper lip feature group, a lower lip feature group, a mouth feature group, a left ear feature group, a brow ridge feature group, a front hairline feature group, and a top head contour feature group.

According to a further aspect, a system is provided that is configured to execute the method of gesture-based editing of a 3D model of a real target. Such system may comprise one or more processors configured to execute machine-readable instructions, a memory for storing machine-readable instructions and data implementing the method of gesture-based editing of a 3D model of a real target, and an input/output interface connected to the one or more processors to allow a user to interact with the system. The input/output interface may include a display. The one or more processors are connected to the memory so as to be configured to execute the machine-readable instructions stored in the memory, wherein the method of gesture-based editing of a 3D model may comprise the following steps:

selecting a 2D projected view of a 3D default model, the 3D model comprising an overall set of vertices, wherein a plurality of subsets of the overall set of vertices form a plurality of 3D feature groups, each 3D feature group comprising an ordered set of feature group points that are associated with a respective specific feature of the default model, selecting a 2D image of the real target which corresponds to the selected 2D projected view of the default model and displaying the selected 2D image of the real target on the display, acquiring at least one line traced by a user over the display that follows at least one real specific feature of the real target visible in the 2D image which correspond to at least one specific feature group, identifying an ordered set of user points belonging to the at least one traced line, matching the user points against the feature group points of the at least one specific feature group in a transformed 2D space of first transformed coordinate L and second transformed coordinate Th, where the first transformed coordinate L of a point is a normalized length in a Cartesian coordinate system of the point in its ordered set of points joined by segments, and the second transformed coordinate Th of the point is an angle of discrete vector difference in the Cartesian coordinate system between two discrete successive vectors respectively following and preceding the point in its ordered set, wherein a subset of user points are identified as best matches of the feature group points of the at least one specific feature group, and updating the 3D default model by applying to the feature group points of the at least one specific feature group 3D geometric difference vectors calculated for each pair of a feature group point and a respective user point identified as best match of such feature group point.

According to an additional aspect, the input/output interface may further include one or more of the following: a keyboard, a pointing device, a port configured to acquire images, and one or more cameras connected to the processor. The processor may be configured to acquire at least one gesture of the user inputted through the user interface.

According to another aspect, the system can further comprise a robotic arm and it can be optionally configured to plan hair transplantation procedures.

The methods and systems according to the present disclosure are notably effective, besides simple, reliable, fast and comfortable for the users.

Other and further objects and advantages disclosed will become apparent from the following detailed description when read in view of the accompanying figures.

BRIEF DESCRIPTION OF THE DRAWINGS

It should be noted that the drawings are not to scale and are intended only as an aid in conjunction with the explanations in the following detailed description. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements and have been solely selected for ease of recognition in the drawings. Features and advantages of the present disclosure will become appreciated as the same become better understood with reference to the specification, claims, and appended drawings wherein:

DETAILED DESCRIPTION OF THE PREFERRED EMBODIMENTS

In the following Detailed Description, reference is made to the accompanying drawings that show by way of illustration some examples of embodiments in which the invention may be practiced. In this regard, directional terminology, such as "right", "left", "front", "back", "top", "vertical", etc., are used with reference to the orientation of the Figure(s) being described. Because components, elements or embodiments of the present invention can be positioned or operated in a number of different orientations, the directional terminology is used for purposes of illustration and is in no way limiting. It is to be understood that other embodiments may be utilized and structural or logical changes may be made without departing from the scope of the present invention. The following description, therefore, is not to be taken in a limiting sense, and the scope of the present invention is defined by the appended claims.

Embodiments of the methods of the present disclosure are implemented using computer software, firmware or hardware processing means, including processors, microprocessors, microcontrollers, and DSPs configured to execute machine-readable instructions. Various programming languages and operating systems may be used to implement the methodology described herein.

In the cosmetic surgery field, equipment showing on a display the future results of the scheduled cosmetic surgery through 3D models of patients improves patient confidence on a positive outcome of the procedure. Examples of such cosmetic surgery are hair transplantation procedures. In hair transplantation in particular, it would be useful if the physician was able to propose potential visual appearances and aesthetic outcomes to a patient, along with a discussion of the time and/or cost associated with each proposed treatment plan. In this manner the patient would be able to see what he/she may look like in each of the scenarios discussed, thus reducing the chances of a patient misunderstanding what the physician may be trying to convey to a patient. Hair transplantation may be carried out manually, or using automated (including robotic) systems or computer-controlled systems, such as those described, for example, in the commonly owned U.S. Pat. No. 7,962,192, which is incorporated herein by reference. Such systems may be provided with the aforementioned equipment, such as one or more displays, for planning and showing the future results of hair transplantation on patient's head. In other instances, the displays may be stand-alone systems. Examples of known equipment and methods for use in the planning of hair transplantation procedures are additionally described in commonly owned U.S. Pat. No. 7,806,121 and US Patent Publication No. 2014/0261467, both incorporated herein by reference.

Other procedures that require a model of the patient's body surface and parts, including, facial and head features, for example, various cosmetic and dermatological procedures involving treatment planning (e.g., plastic surgery, wrinkle removal or reduction, injections of cosmetic substances, skin grafting procedures, correction or removal of birth mark defects, facial reconstruction, rhinoplasty, contouring of the eyes or lips, remodeling of ears, nose, eye-lids or chins, facial rejuvenation, laser skin resurfacing, skin tightening, etc.) may benefit from the systems and methods described herein. One example of applicability of the present disclosure is in diagnostic skin imaging for cosmetic or other medical purposes, for example skin grafting or tattoo removal. For convenience of description, the following description will be discussed by example in reference to hair transplantation procedures. It should be noted, however, that such description is for the purposes of illustration and example only and is not intended to be exhaustive or limiting.

Figure 1:
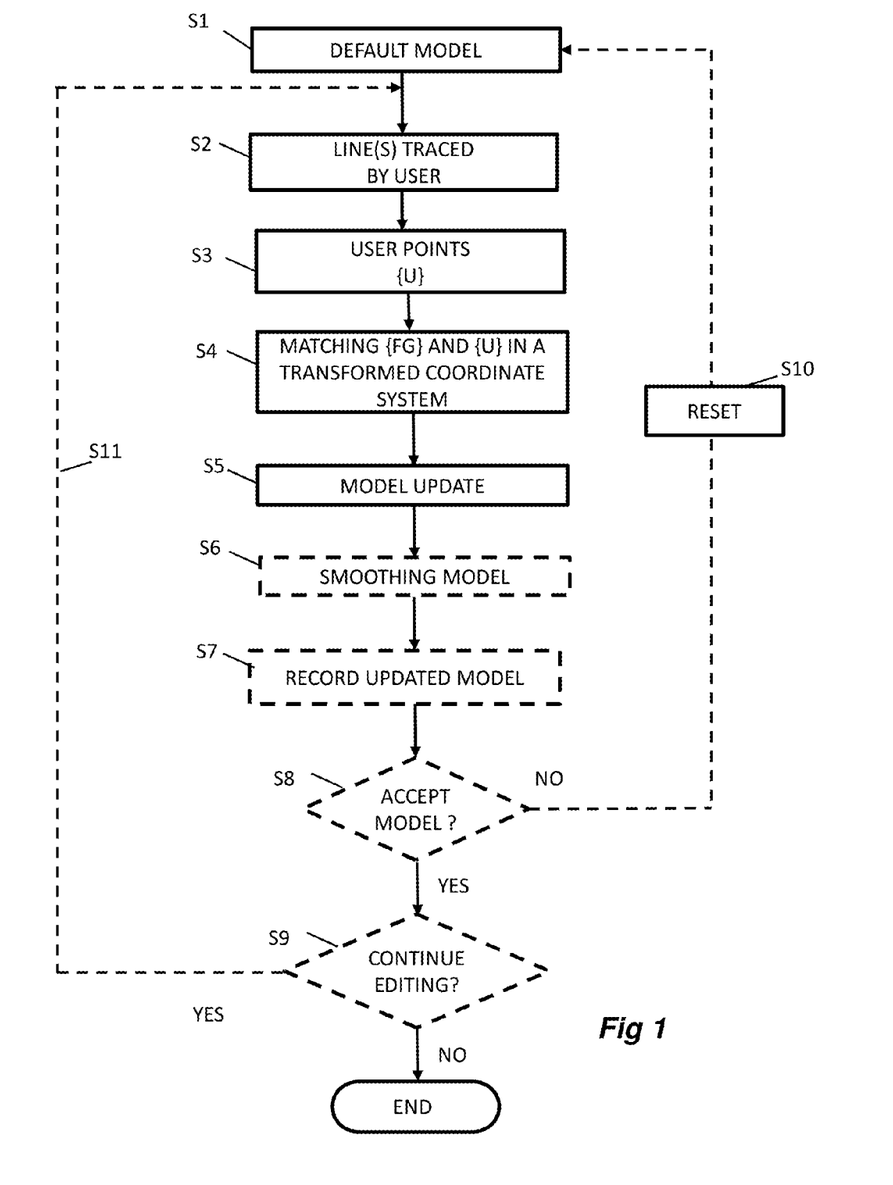
FIG. 1 is a flow chart illustrating an embodiment of the method according to the present disclosure.

FIG. 1 is a flow chart illustrating an example of an embodiment of the method according to the present disclosure for editing 3D models of patients' heads for use in medical/cosmetic applications, such as in the planning of hair transplantation procedures. However, as already stated, it must be understood that the gesture-based editing of 3D models according to the present disclosure may be also used for editing 3D models of other real targets, either different parts of a person's body or even objects, and/or in different applications, still remaining within the scope of protection of the present disclosure.

Figure 2:
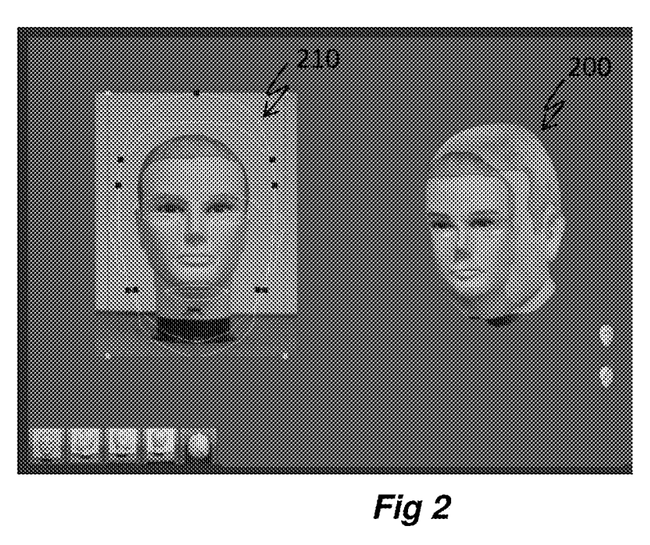
FIG. 2 shows an example of a first user interface displayed on a display during execution of the method of FIG. 1.

As a starting point S1 a default 3D head model which will be referred to as the default model, similar to the model shown in FIG. 2 and a first perspective view of which is indicated by the reference numeral 200 is used. FIG. 2 shows an example of a 2D front view 210 of the default model. The default model may be represented as an overall set of vertices on a 3D surface mesh. In particular, the default model may be created from any available 3D modeling suite.

A plurality of 3D sets of vertices are associated with the default model, wherein the vertices of each set are located along a line delineating a head model feature. These 3D feature sets of vertices may correspond to respective subsets of vertices picked from the overall set of vertices of the default model. Accordingly, a 3D feature set of vertices may be associated to a specific facial/cranial feature, e.g. the jaw line, of the default model.

Each 3D feature set of vertices may define a specific facial and/or cranial feature of the head model in at least one 2D projected view (usually in at least two different projected views) of five orthogonal 2D projected views of the default model, for example, front, back, left, right, and top views. For instance, the jaw line may be defined by the respective 3D feature set of vertices in the 2D front, left, and right views. Each 3D feature set of vertices is referred to as a feature group, and its vertices are also referred to as feature group points. Optionally, distances between vertices of a feature group are typically on the order of 0.2 to 0.5 units in the texture coordinates, however, other appropriate distances may be used.

Other embodiments of the methods according to the present disclosure may consider a different number and orientation of 2D projected views of the default model, provided that the 2D projected views are at least two. For instance, other embodiments of the methods according to the disclosure may consider six orthogonal 2D projected views of the default model, for example, front, back, left, right, top and bottom views.

Figure 3:
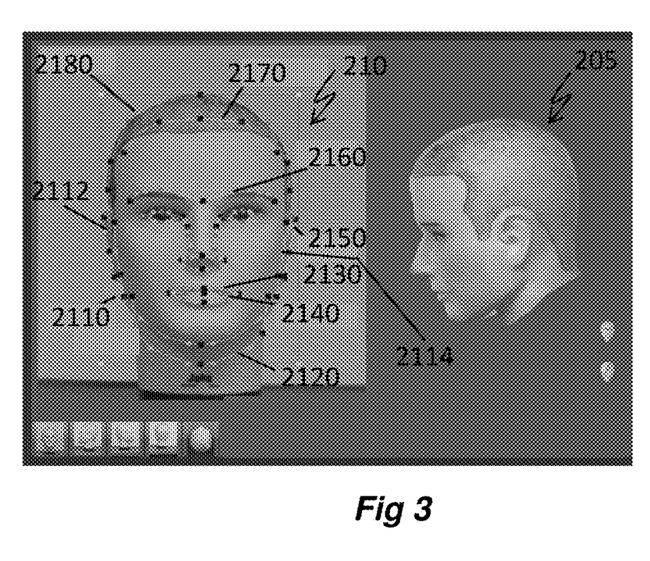
FIG. 3 shows an example of a second user interface displayed on a display during execution of the method of FIG. 1.

By way of example, and not by way of limitation, FIG. 3 shows a second perspective view, indicated by the reference numeral 205, of the default model, as well as the 2D front view 210 of the default model on which several feature groups are highlighted. Vertices of feature groups in FIG. 3 (as well as in FIGS. 2 and 4) are represented as square dots. In FIG. 3, the following feature groups define respective specific facial/cranial features of the head model in the 2D front view 210 of the default model shown in FIG. 3: the jaw line feature group 2110 (delimited in the 2D front view 210 by end vertices 2112 and 2114); the laryngeal prominence feature group 2120 (defining the line passing through the protrusion of the thyroid cartilage); the upper and lower lip feature groups 2130 and 2140 (or their combination as a mouth feature group 2130-2140); the left ear feature group 2150; the brow ridge feature group 2160; the front hairline feature group 2170; and the top head contour feature group 2180.

In order to quickly and accurately modify the default model into a fitting model better representing a real target, especially if such default model represents some organic form, e.g. a patient's head, that cannot be easily represented by simple geometry, the method according to the present disclosure deforms the feature groups so as to create the fitting model that accurately represents the real target, e.g. the patient's real facial/cranial structure.

In reference to one general example of the methodology shown in FIG. 1, in step S2, a 2D projected view of the default model is selected and a 2D image of the patient's head (e.g., a photograph) positioned substantially according to the selected 2D projected view of the default model is displayed, for example, on a monitor or display. Optionally, in some embodiments, the selected 2D projected view of the default model may also be displayed. For example, such 2D projected view may be selected either automatically by the system or by the user from the group of the previously listed five orthogonal 2D projected views. The user traces over the display of the above-mentioned 2D image to follow an actual specific facial and/or cranial feature of the patient visible in the 2D image. In particular, the user, e.g. a surgeon, may trace lines over the display by interacting with at least one pointing device, such as a mouse and/or the same display when the latter is a touch-screen display. Advantageously, as stated, step S2 may include showing a photograph of the same 2D projected view of the patient's head (that can be preliminary stored in a memory) that is superimposed to the 2D projected view (optionally selectable by the user) of the default model, so as to assist the user in tracing lines.

When the user traces a line over the display, he or she may input the specific facial/cranial feature of the default model to which such traced line corresponds (e.g. jaw line or top head contour), by selecting the feature, for example, from a list of icons displayed in a menu on the display. Alternatively, the method could automatically recognize the specific facial/cranial feature of the default model to which such traced line corresponds, e.g. on the basis of the least distance of the pair of end points of the traced line from the pair of end vertices of all possible feature groups defining the specific facial/cranial features of the default model visible in the selected 2D projected view displayed on the display. Other embodiments of the method according to the present disclosure may allow a user to trace two or more lines over the display, wherein said two or more traced lines follow a combination of two or more actual specific facial/cranial features of the patient and correspond to a combination of two or more specific facial/cranial features of the default model visible in the selected 2D projected view displayed on the display.

Figure 4:
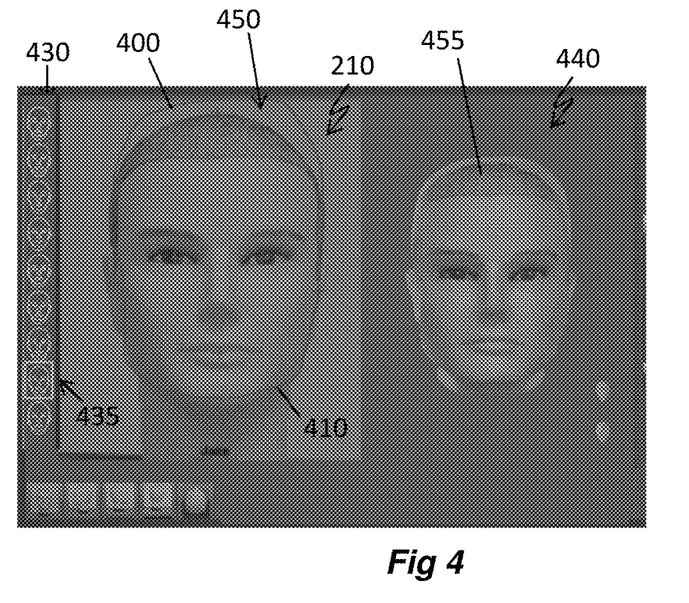
FIG. 4 shows an example of a third user interface displayed on a display during execution of the method of FIG. 1.

Having acquired the line traced by the user, in step S3 the system identifies an ordered set of points, which are associated with the traced line. Such points may be considered, for example, as mouse positions for that traced line, i.e. they are identified by Cartesian coordinates in two dimensions. FIG. 4 shows an example of this, wherein the user has traced a line 400 following the top contour of the head of the patient and also a line 410 the jaw line of the patient over the display of the 2D front view 210 of the default model. Furthermore, FIG. 4 shows a vertical menu 430 including a list of icons of specific facial/cranial feature of the default model to which a traced line may correspond, wherein the icon 435 (related to the top head contour) has been highlighted because it has been selected by the user as the feature of the default model to which the traced line corresponds. In various embodiments, each point (except the first one of the traced line) may be checked against the previous point to ensure that it is at least some small distance from its nearest neighbor, wherein may be, for example, in the range of 0.001 to 0.01 in the texture coordinates. In such implementations, the method limits the number of ordered points stored for a traced line still ensuring that the default model will be modified into a fitting model accurately representing the real target (according to the accuracy of the traced line). Step S3 results in a list of pairs of display coordinates (i.e. mouse positions over the screen) that will be referred to as user points. There may be one to two hundred points representing the line traced over the selected 2D projected view following a real feature of the patient's head. In general, the ratio of the number of user points to the number of feature group points ranges from 20 to 5000.

Figure 5:
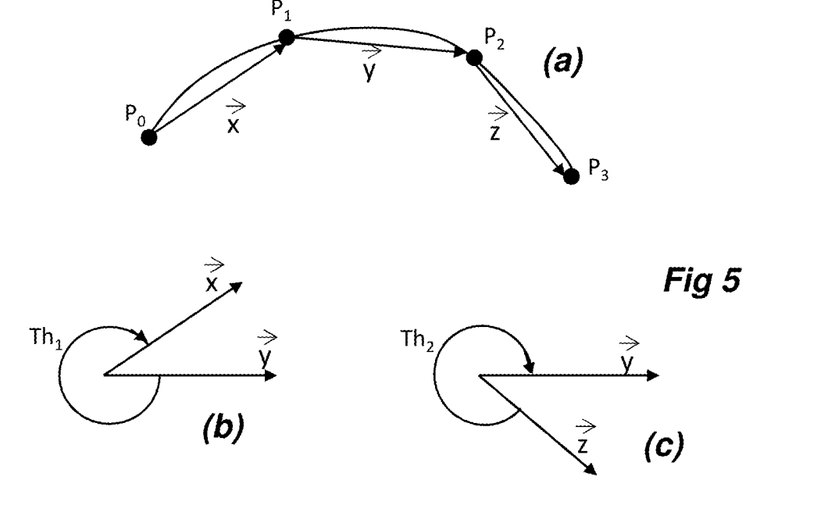
FIGS. 5(a)-(c) show examples of execution of first portions of the matching step of the method of FIG. 1.

Step S4 matches the user points of the traced line against the feature group points of the respective feature group of the default model (i.e. of the Feature group defining the specific facial/cranial feature of the default model to which the traced line corresponds) in the selected 2D projected view in a transformed 2D space. For example, matching of step S4 may include transforming the Cartesian coordinates (X, Y) of the user points into a custom coordinate system (L, Th), where L is the arc length percent along the traced line from the start of the line versus the total length of the trace (i.e. L is the normalized length along the ordered set of user points, joined by segments, from the first point of the traced line to the user point of which L is computed), and Th is the angle of the discrete vector difference between two discrete successive vectors, respectively following and preceding the user point of which Th is computed, as it will be better described with reference to FIG. 5. The Cartesian coordinates (X, Y) of the each vertex of the respective feature group is transformed into the same custom coordinate system (L, Th) as well.

In particular, custom coordinates (L, Th) may be calculated in two successive sub-steps, wherein L is calculated for each feature group point and each user point in the first sub-step, while Th is calculated in the second sub-step (following the first sub-step) for each feature group point and for all or part of the user points, as it will be explained later on.

Assuming that any one of a traced line or a feature of the default model (i.e. a feature group) includes an ordered set of N points $P_i$ (with i=0, 1, . . . , N−1):

$$\{P_0, P_1, \ldots, P_i, \ldots P_{N-1}\}$$

$L_i$ for point $P_i$ is the normalized length along the ordered set of points, joined by segments, from the first point $P_0$ of the ordered set to point $P_i$. As an example, FIG. 5a shows a line that can be any one of a traced line or a feature group, including four points $$\{P_0, P_1, P_2, P_3\}$$

whereby the values $L_i$ (i=0, 1, 2, 3) of L for these four points are as follows:

$$L_0 = D(P_0, P_0)/(D(P_3, P_2) + D(P_2, P_1) + D(P_1, P_0)) = 0$$

$$L_1 = D(P_1, P_0)/(D(P_3, P_2) + D(P_2, P_1) + D(P_1, P_0))$$

$$L_2 = (D(P_2, P_1) + D(P_1, P_0))/(D(P_3, P_2) + D(P_2, P_1) + D(P_1, P_0))$$

$$L_3 = (D(P_3, P_2) + D(P_2, P_1) + D(P_1, P_0))/(D(P_3, P_2) + D(P_2, P_1) + D(P_1, P_0)) = 1$$

where D(Q, R) returns the Cartesian distance between points Q and R.

Figure 6:
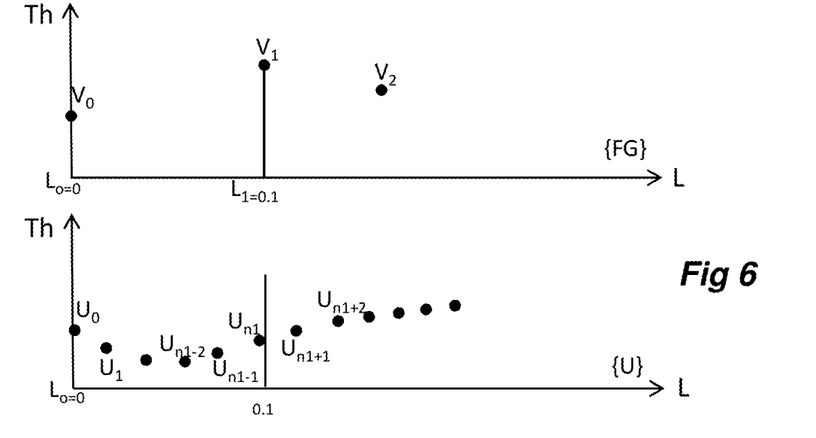
FIG. 6 shows an example of execution of another portion of the matching step of the method of FIG. 1.

As stated, the L coordinate is computed over all feature group points, hereinafter also referred to as {FG}, and all user points, hereinafter also referred to as {U}. This procedure anchors the relatively many user points to the relatively few feature group points. Namely, the L coordinate of the first point in {FG}, i.e. $L_0$ in {FG}, is matched with the L coordinate of the first point in {U}, i.e. with $L_0$ in {U}, since they are both equal to 0 (zero). With reference to FIG. 6, assuming that the L coordinate of the second point in {FG}, i.e. $L_1$ in {FG}, is equal to 0.1, step S4 finds the point in {U} having the L coordinate that it is closer to $L_1$=0.1 than its neighbors in {U}. In general, such point in {U} is not the second point $U_1$ of the ordered set of {U}, and its index in {U} may be indicated as n1 (where n1 is an index between 0 and the total number of points in {U}), whereby $L_i = L_{n1}$ in {U} is closer to 0.1 than its neighbors in {U}. Then, step S4 anchors such n1-th point, having L coordinate equal to $L_{n1}$ in {U}, to the second point in {FG} having L coordinate equal to $L_1$ in {FG}; in other words, step S4 skips several points in {U} to arrive at n1-th point, having L coordinate equal to $L_{n1}$ in {U}.

At this stage, the first point (i.e. vertex) in {FG} having L coordinate equal to $L_0$ still corresponds to the first point $V_0$ in the ordered set of feature group points stored in Cartesian coordinates (X, Y); similarly, the second point in {FG} having L coordinate equal to $L_1$ still corresponds to the second point $V_1$ in the set of feature group points stored in Cartesian coordinates (X, Y), and so on. The first point $U_0$ in {U} having L coordinate equal to $L_0$ still corresponds to the first point in the ordered set of user points stored in Cartesian coordinates (X, Y); however, the point in {U} having L coordinate closest to $L_1$ is the n1-th point $U_{n1}$ in the set of user points stored in Cartesian coordinates (X, Y), where n1 is an index between 0 and the total number of points in {U}. Similarly, step 4 finds (N−2) points $U_{n2}, \ldots U_{nN-1}$ in {U} (where N is the number of points in the ordered set of feature group points) having the L coordinates respectively closer to the L coordinates of the remaining (N−2) points of the feature group points $V_2, \ldots, V_{N-1}$, hence anchoring each one of these N points $\{U_0, U_{n1}, \ldots, U_{ni}, \ldots U_{nN-1}\}$ found in {U} to a respective one of the N points $\{V_0, V_1, \ldots, V_i, \ldots V_{N-1}\}$ of the feature group.

This anchoring is a sort of provisional matching of the many user points to the relatively few feature group points (wherein a subset of user points are anchored to the feature group points on the basis of the L coordinate only). In order to guarantee optimal curve matching, such provisional matching is then refined by taking into account how successive points in each one of the two sets of points (namely feature group points and user points) move relative to each other and by minimizing any movement difference between the two sets of points in correspondence to the anchored pairs of points identified on the basis of the L coordinate only. To this end, step S4 may take into account the second custom coordinate Th as follows.

For each one of the feature group points $\{V_0, V_1, \ldots, V_i, \ldots V_{N-1}\}$, angle Th is calculated as follows:

$Th_0 = \arccos(InnerProduct((V_1 - V_0), (V_1 - V_0))) = 0$ $Th_1 = \arccos(InnerProduct((V_2 - V_1), (V_1 - V_0)))$ $Th_2 = \arccos(InnerProduct((V_3 - V_2), (V_2 - V_1)))$

...

$Th_i = \arccos(InnerProduct((V_{i+1} - V_i), (V_i - V_{i-1})))$

...

wherein (R−Q) indicates the 2D vector from point Q to point R, and wherein the angle $Th_{N-1}$ of the last point $V_{N-1}$ in the ordered set of feature group points is just equal to the angle $Th_{N-2}$ of the last-but-one point $V_{N-2}$. An example of the computation of angle Th is shown in FIGS. 5b and 5c for $Th_1$ and $Th_2$ related to points $P_1$ and $P_2$ belonging to the line of FIG. 5a, wherein the 2D vectors from point $P_0$ to point $P_1$, from point $P_1$ to point $P_2$ and from point $P_2$ to point $P_3$ are indicated respectively by $\vec{x}$, $\vec{y}$ and $\vec{z}$. Similarly, angle Th of each point of the subset $\{U_0, U_{n1}, \ldots, U_{ni}, \ldots U_{nN-1}\}$ of user points (which have been anchored to the feature group points on the basis of the L coordinate only) is calculated as follows:

$Th_0 = \arccos(InnerProduct(U_{n1} - U_0, U_{n1} - U_0)) = 0$ $Th_{n1} = \arccos(InnerProduct(U_{n2} - U_{n1}, U_{n1} - U_0))$ $Th_{n2} = \arccos(InnerProduct(U_{n2} - U_{n2}, U_{n2} - U_{n1}))$

...

$Th_{ni} = \arccos(InnerProduct((U_{ni+1} - U_{ni}), (U_{ni} - U_{ni-1})))$

...

again, wherein the angle $Th_{nN-1}$ of the last point $U_{nN-1}$ in the ordered set of user points is just equal to the angle $Th_{nN-2}$ of the last-but-one point $U_{nN-2}$.

Refinement of the provisional matching of the subset of User points anchored to the feature group points on the basis of the L coordinate uses the points $\{U_0, U_{n1}, \ldots, U_{ni}, \ldots U_{nN-1}\}$ of this subset as starting points for a recursive best match search. For the sake of simplicity, in the following reference is made only to the second point $U_{n1}$ of the subset of User points and respective second vertex $V_1$ of the feature group points, but this is made without impairing generality of the approach for any one of the points $\{U_0, U_{n1}, \ldots, U_{ni}, \ldots U_{nN-1}\}$ of the subset of user points, for which similar considerations apply. Thus, with reference to FIG. 6, considering the second point $U_{n1}$ in the subset, that is not, in this particular example, the second point $U_1$ of the whole ordered set $\{U\}$ of user points, in a first recursion of the recursive best match search, step S4 computes the custom coordinates of its two neighbors $U_{n1-1}$ and $U_{n1+1}$ in $\{U\}$, namely calculating $(L_{n1-1}, Th_{n1-1})$ and $(L_{n1+1}, Th_{n1+1})$, and it then compares the three distances of the three points $U_{n1-1}$, $U_{n1}$ and $U_{n1+1}$ from the respective second vertex $V_1$ of the feature group points (to which user point $U_{n1}$ has been anchored on the basis of the L coordinate only) to each other, wherein such distances are calculated in the custom coordinate system (L, Th) according to the least square distance criterion. In particular, assuming that a generic k-th user point $U_k$ in $\{U\}$ has custom coordinate $(L_k, Th_k)$ and that the respective h-th vertex $V_h$ in $\{FG\}$ has custom coordinate $(L_h, Th_h)$, the distance function D computes the difference squared, similarly to a Cartesian distance:

$D^2 = (Th_h - Th_k)^2 + (L_h - L_k)^2$.

If the outcome of this comparison is that point $U_{n1}$ is indeed the closest to vertex $V_1$, then recursion of the best match search is stopped and point $U_{n1}$ is identified as the best match of vertex $V_1$. However, if the first recursion of the recursive best match search ascertains that point $U_{n1-1}$ preceding point $U_{n1}$ in $\{U\}$ is the closest one, then the recursive best match search is applied to a novel triplet on the left of point $U_{n1}$ in FIG. 6 (i.e. towards the preceding points) and step S4 performs a second recursion of the recursive best match search looking at the three successive points centered in $U_{n1-1}$, for example, by comparing the three distances—still calculated in the custom coordinate system (L, Th)—of the three points $U_{n1-2}$, $U_{n1-1}$ and $U_{n1}$ from the vertex $V_1$. Similarly, if the first recursion of the recursive best match search ascertains that point $U_{n1+1}$ following the starting point $U_{n1}$ is the closest one, then the recursive best match search is applied to a novel triplet on the right of point $U_{n1}$ in FIG. 6 (i.e. towards the following points) and step S4 performs a second recursion of the recursive best match search looking at the three successive points centered in $U_{n1+1}$, for example, by comparing the distances—again calculated in the custom coordinate system (L, Th)—of the three points $U_{n1}$, $U_{n1+1}$ and $U_{n1+2}$ from the vertex $V_1$. In both cases, recursion stops if the central point of the triplet, for example, $U_{n1-1}$ or $U_{n1+1}$, is ascertained as the closest to the vertex $V_1$ and such central point of the triplet is identified as the best match of vertex $V_1$, otherwise step S4 performs a third recursion of the recursive best match search looking at the three successive points centered in the closest point of the triplet considered in the preceding second recursion. It will be appreciated by those skilled in the art that step S4 similarly may perform further recursion(s) of the recursive best match search until it ascertains that the central point of a triplet, that is a sort of best guess match, is indeed the closest point of the triplet to the vertex $V_1$ and such central point of the triplet is identified as the best match of vertex $V_1$. In other words, such recursive best match search is a form of binary search.

Other embodiments of the method according to the disclosure may execute the recursive best match search looking at three successive points at an end point (instead of the central point) which coincides with the point that the preceding recursion has recognized as closest to the vertex of the feature group under consideration.

Further embodiments of the method according to the disclosure may execute the recursive best match search looking at more than three points, e.g. four or five points, the distances of which from the vertex of the feature group under consideration are to be compared to each other. In some embodiments, the number of such points, the distances of which are to be compared, could vary during several recursions, such as from one recursion to another one, e.g.

this number could decrease from the first recursion to the subsequent ones until it is reduced down to a lower limit.

In other embodiments of the method according to the disclosure, step S4 may first compute the custom coordinate system (L, Th) for all the points of the whole ordered set {U} of user points and then may search for the user point closest to each point (i.e. vertex) of the feature group points by comparing the distances—calculated in the custom coordinate system (L, Th)—of at least some or all the user points from the considered feature group point.

In other words, in such embodiment step S4 transforms Cartesian coordinates of both points {U} belonging to the line traced by the user and points {FG} of the respective feature group (i.e. of the specific facial/cranial feature of the default model to which such traced line corresponds) to custom coordinates (L, Th) where it matches the appropriate user point of the line traced by the user to each feature group point according to a least distance criterion (in the custom coordinate system). This entails a number of advantages when compared to a proximity-based approach applied in the Cartesian coordinate system, since the transform-based approach according to the disclosure allows the user to define features on multiple scales. For instance, a side profile of a person's nose and mouth contains features at coarse scale (forehead portion of the curve) and fine scale (curvature of the nose, mouse/lips): a purely proximity-based approach for such a feature group would generally mismatch contour points near portions containing detailed variations, while the transform-based approach according to the disclosure allows the user to better fit the line traced by the user to the respective feature group.

Figure 7:
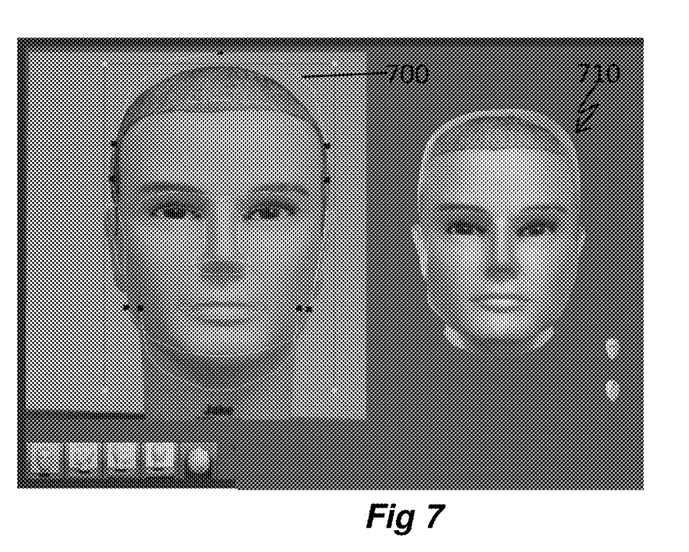
FIG. 7 shows an example of a fourth user interface displayed on a display during execution of the method of FIG. 1.

Again with reference to FIG. 1, step S5 comprises updating (i.e. modifying) the default model. In one example, in order to update the model appropriately, step S5 takes each matched pair of user point and respective feature group point (wherein the user point has been identified as the best match of the respective feature group point) and computes the related 3D geometric difference vector (dx, dy, dz) in (the Cartesian system of) the selected 2D projected view, wherein difference vector components that do not lie on the view plane are ignored (zeroed). Thus, step S5 applies the 3D geometric difference vectors to each feature group point of the default model. In other words, as shown in FIG. 7, step S5 replaces the original feature group of the top head contour (indicated with reference numeral 2180 in FIG. 3) with the subset 700 of user points (of the line traced by the user for drawing the patient's top head contour) matching the feature group points (of top head contour feature group 2180 in FIG. 3) of the default model.

Figure 8:
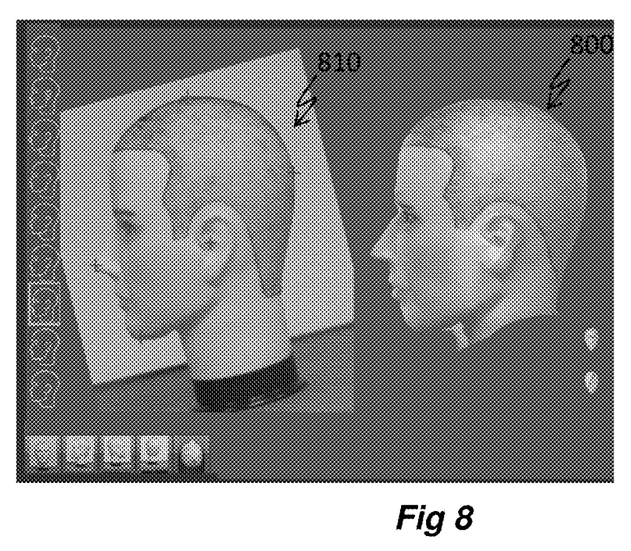
FIG. 8 shows an example of a fifth user interface displayed on a display during execution of the method of FIG. 1.

The subset of user points replacing the former feature group 2180 has sharp corners, since it is linearly interpolated (as any other feature group). Therefore, next optional step S6 in FIG. 1 treats the updated model (fitting model) as an intermediate 3D model and applies smoothing to such intermediate model for achieving the smoothed effect and obtaining an updated fitting model 700 (such smoothing of the fitting model is evident in perspective view 710 of the fitting model in FIG. 7). In this regard, several smoothing techniques could be employed, such as those based on cubic splines, Bezier curves or Gaussian kernel convolution. FIG. 8 shows a left projected view of the fitting model resulting from smoothing of step S6, as well as a perspective view 800 of the same fitting model.

Advantageously, step S6 may apply any local distortion between the default model and the fitting model to the texture map grabbed from the original patient's photograph(s) to get a realistic end model. For instance, in FIG. 4, wherein an exaggerated patient's top head contour line 400 has been traced by the user to include portions 450 of image background, the background texture 455 is added to the fitting model, a perspective view 440 of which is also shown.

In step S7, the updated smoothed model is optionally recorded. The fitting model may be displayed on a display so that the user can appreciate the update of the default model resulting from the modifications caused by the traced line.

In some embodiments, the default may be to accept the updated default model (the fitting model), as substantially corresponding to the gesture-based edited 3D default model. In other embodiments, in step S8, the method according to the disclosure may optionally allow for a feedback from the user on the resulting fitting model. If the user is satisfied, by default or by inputting an acceptance command, and want to accept the resulting model without any further modifications, then the method ends (see "Yes" branch exiting from step S8 in FIG. 1 followed by "No" branch exiting from the block "Continue Editing"). Otherwise, if the user does not want to accept the resulting fitting model ("No" branch exiting from step S8), the method allows the user in step S8 to input a non-acceptance command, thus allowing to reset (step S10) and start over again either from the original default model (returning back to step S1) or, in some implementations, resetting to some previous (e.g., intermediate) state or form of the model and repeat any necessary steps. In other words, in one aspect of the invention, resetting may comprise undoing step S5, and rolling back to the former default model (or to a previously obtained fitting model), and the method is repeated from step S2 starting from the former default model (or from a previously obtained fitting model). In another aspect, the method may optionally allow for feedback from the user as to whether he/she desires to continue editing the fitting model. If the user does not desire to edit the fitting model further, the user selects the "No" branch exiting from step S9. Should further editing be desired (the "Yes" branch exiting from S9), the user can modify or fine-tune the just obtained fitting model (via S11) by repeating the method, for example, from step S2 but setting as a starting default model the just obtained fitting model, including the updated feature group(s). Modification or fine-tuning of the fitting model may comprise the user tracing another line over the display, input another specific facial/cranial feature of the default model to which such traced line corresponds (e.g. jaw line or top head contour), or by selecting another feature, for example, from a list of icons displayed in a menu on the display. In some implementations, modification or fine-tuning of the fitting model may comprise editing the previously traced line by the user, applying one or more alternative or additional smoothing techniques, removing the application of one or more smoothing techniques, texturing, or the combination of one or more modification or fine-tuning techniques that result in a more accurate edited 3D default model. In some aspects of the disclosure, modification may occur in step S11, without repeating the method from step S2, for example, by modifying the fitting model to incorporate an alternative texture grabbed from the 2D image. Additionally, alternative 3D model editing techniques known to those in the art may be applied in combination with the gesture-editing techniques described hereinbefore. It will be apparent that there are numerous orders and methodologies which may be applied to the accepting, not accepting, or selecting to further modify the fitting model, and is this regard the application should not be limited in this regard.

Figure 9:
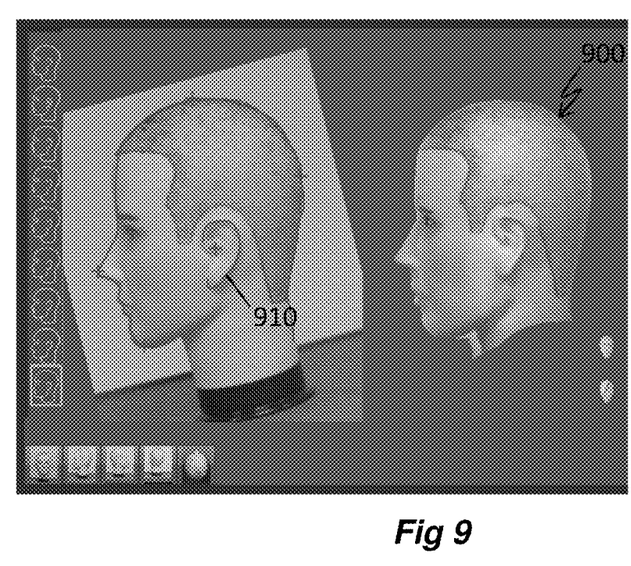
FIG. 9 shows an example of a sixth user interface displayed on a display during execution of the method of FIG. 1.

For instance, in a second repetition of the method the user could trace a line 410 following the patient's jaw line shown in FIG. 4, and in a third repetition the user could trace a line 910 following the patient's right ear contour shown in FIG. 9, thus obtaining a final fitting model (a perspective view 900 of which is also shown in FIG. 9).

Advantageously, the initial default model and any or all the subsequently obtained fitting model may be stored, along with the history of model deformations the user performs, in a memory. Also, the custom coordinates (L, Th) of all the feature group points of all the feature groups of the initial default model could be stored in the memory, although this is not essential to the methodology disclosed, since cost of computation of the custom coordinates (L, Th) for all the feature group points of one (or more) feature group(s) is not burdensome.

The technique described here could be useful for a wide range of 3D model applications that are normally not achievable or difficult to achieve through currently available modeling techniques, such as those used in CAD and gaming applications.

As will be appreciated by those skilled in the art, the methods of the present disclosure may be embodied, at least in part, in software and carried out in a computer system or other data processing system. Therefore, in some exemplary embodiments hardware may be used in combination with software instructions to implement the present disclosure.

A machine-readable medium may be used to store software and data which causes the system to perform methods of the present disclosure. The above-mentioned machine-readable medium may include any suitable medium capable of storing and transmitting information in a form accessible by processing device, for example, a computer. Some examples of the machine-readable medium include, but are not limited to, magnetic disc storage, flash memory device, optical storage, random access memory, etc.

Figure 10:
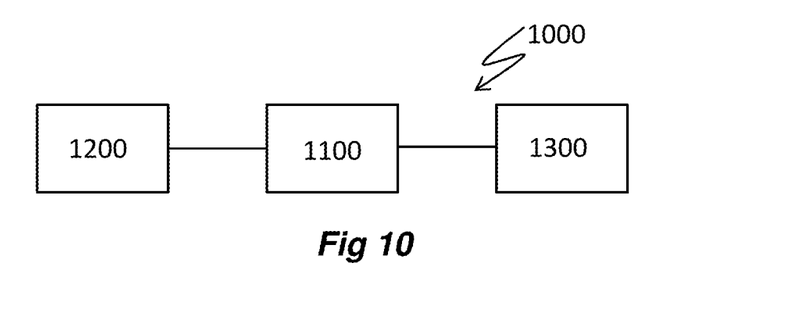
FIG. 10 illustrates a system according to the present disclosure.

With reference to FIG. 10, an embodiment of a system 1000 configured to execute the methods for editing 3D models using gesture generated traces according to the present disclosure may comprise: one or more processor 1100 for executing the methods according to the disclosure, which one or more processor 1100 is connected to memory 1200, storing machine-readable instructions and data such as default models of targets and fitting models resulting from execution of the method according to the disclosure, and input/output interface 1300 for allowing a user to interact with the system, for example, to input commands, patient's photographs, or to trace lines over patient's photographs or other images. The one or more processor 1100 may include processors, microprocessors, microcontrollers, and DSPs configured to execute machine-readable instructions. By way of example, and not limitation, a processor (image processor) may be a controller or any type of personal computer ("PC"). Alternatively, the processor (image processor) may comprise an Application Specific Integrated Circuit (ASIC) or Field Programmable Gate Array (FPGA). The processor may also include one or more non-transitory storage media (which may take the form of, but is not limited to, a magnetic storage medium; optical storage medium; magneto-optical storage medium; read only memory; random access memory; erasable programmable memory; flash memory; and so on). The above-described processor could be used in conjunction with various partially automated and fully automated (including robotic) hair transplantation and treatment systems and devices, including but not limited to systems for hair harvesting, or hair transplantation. The input/output interface 1300 may include one or more components for transmitting output to and/or receiving input from one or more other components (such as one or more displays, touch screens, keyboards, mice, track pads, track balls, pointing devices, styluses, pens, printers, speakers, cameras, video cameras, and so on). The interface may include hardware ports (including a port configured to acquire images) cables, leads, and other data transmission means, or it may comprise a computer program.

The systems and methods of the present disclosure are especially useful when implemented on, or integrated with, an automated system, for example, a robotic system comprising a robotic arm. In particular, such automated system can be a hair harvesting, implantation or hair transplantation system.

The various embodiments described above are provided by way of illustration only and should not be construed to limit the claimed disclosure. These embodiments are susceptible to various modifications and alternative forms, and it should be understood that the invention generally, as well as the specific embodiments described herein, cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. Further, those skilled in the art will recognize that the devices, systems, and methods disclosed herein are not limited to one field, such as hair restoration, but may be applied to any number of fields. The description, therefore, is not to be taken in a limiting sense, and the scope of the present disclosure is defined by the appended claims.

It will be further appreciated by those skilled in the art that the disclosure is not limited to editing of 3D models of heads not to medical/cosmetic applications, and that the gesture-based editing of 3D models according to the present disclosure may be also used for editing models of other real targets, either different parts of a person's body or even objects, and/or in different applications availing of computer graphics for processing and showing the appearance of a person or of an arrangement, still remaining within the scope of protection of the present disclosure.

What is claimed is:

1. A method of gesture-based editing of a 3D model of a real target comprising the following steps:

selecting a 2D projected view of a 3D default model, wherein the 3D default model comprises an overall set of vertices, wherein a plurality of subsets of the overall set of vertices forms a plurality of 3D feature groups, each 3D feature group comprises an ordered set of feature group points that are associated with a respective specific feature of the default model;

selecting a 2D image of a real target with a view which corresponds to the selected 2D projected view of the default model, and displaying the selected 2D image of the real target on a display;

acquiring at least one line traced by a user over the 2D image of the real target on the display that follows at least one specific feature of the real target visible in the 2D image which correspond to at least one specific feature group;

identifying an ordered set of user points belonging to the at least one traced line;

matching the user points against the feature group points of the at least one specific feature group in a transformed 2D space of first transformed coordinate L and second transformed coordinate Th, where the first transformed coordinate L of a point is a normalized length in a Cartesian coordinate system of the point in its ordered set of points joined by segments, and the second transformed coordinate Th of the point is an angle of discrete vector difference in the Cartesian coordinate system between two discrete successive vectors respectively following and preceding the point in its ordered set, wherein a subset of user points is identified as a best match of the feature group points of the at least one specific feature group; and updating the 3D default model by applying to the feature group points of the at least one specific feature group 3D geometric difference vectors calculated for each pair of a feature group point and a respective user point identified as best match of such feature group point.

2. The method of claim 1, wherein the updating the default model further comprises smoothing the 3D model for obtaining a fitting model of the real target.

3. The method of claim 2, wherein smoothing is based on one or more techniques selected from the group comprising cubic splines, Bezier curves and Gaussian kernel convolution.

4. The method of claim 2, wherein smoothing includes applying any local distortion between the default model and the fitting model to a texture map grabbed from the 2D image of the real target.

5. The method of claim 1, further comprising displaying the 2D projected view of the 3D default model.

6. The method of claim 1, wherein matching is based on a least distance criterion in the transformed 2D space.

7. The method of claim 6, wherein matching includes:
calculating first transformed coordinate L for each feature group point of the at least one specific feature group and for each user point,
for each feature group point of the at least one specific feature group, identifying the user point having first transformed coordinate L closest to the first transformed coordinate L of the feature group point under consideration, whereby a subset of user points are selected to be provisionally anchored to the feature group points of the at least one specific feature group,
using each point of the subset of user points as starting points for a recursive best match search for each feature group point of the at least one specific feature group, wherein the recursive best match search searches for a user point of the ordered set of user points belonging to the at least one traced line having the least distance from the feature group point in the transformed 2D space of first transformed coordinate L and second transformed coordinate Th, whereby for each feature group point of the at least one specific feature group a user point of the ordered set of user points belonging to the at least one traced line is identified as best match of the feature group point.

8. The method of claim 7, wherein for each feature group point of the at least one specific feature group the recursive best match search includes:
assuming the provisionally anchored user point as guess best match of the feature group point,
selecting a tuple of successive points of the ordered set of user points belonging to the at least one traced line including the guess best match,
comparing distances in the transformed 2D space of first transformed coordinate L and second transformed coordinate Th of the successive points of the tuple from the feature group point, whereby a provisional least distant point having the least distance from the feature group point is identified,
stopping recursion when the provisional least distant point is the guess best match, otherwise assuming the provisional least distant point as guess best match of the feature group point and making another recursion of selecting a tuple of successive points of the ordered set of user points and comparing distances of the successive points of the tuple from the feature group point.

9. The method of claim 8, wherein a tuple of successive points of the ordered set of user points includes three or more points.

10. The method of claim 9, wherein a tuple of successive points of the ordered set of user points includes an odd number of points, wherein the guess best match is a central point of the tuple.

11. The method of claim 1, wherein a ratio of total number of user points to total number of feature group points of the at least one specific feature group ranges from 20 to 5000.

12. The method of claim 1, wherein the 2D projected view is selected from the group comprising five orthogonal 2D projected views including a front view, a back view, a left view, a right view, and a top view.

13. The method of claim 1, wherein the 2D projected view is selected from the group comprising six orthogonal 2D projected views including a front view, a back view, a left view, a right view, a top view and a bottom view.

14. The method of claim 1, wherein the user traces the at least one line by interacting with at least one pointing device.

15. The method of claim 14, wherein the at least one pointing device includes a mouse, a keyboard, a track pad, a track ball, a pointing devices, a stylus, a pen, and/or a touch-screen display.

16. The method of claim 1, wherein acquiring the at least one line traced by a user over the display includes receiving an indication of the at least one specific feature group of the default model to which the at least one traced line corresponds.

17. The method of claim 16, wherein receiving an indication includes selecting the at least one specific feature group of the default model from a list of icons displayed in a menu on the display.

18. The method of claim 1, further comprising providing for user feedback by allowing the user to accept the updated default model, or delete any previous change of the default model, or to further modify the updated default model by setting the updated default model as a new default model and repeating the steps of the method.

19. The method of claim 1, further comprising allowing the user to combine the method with one or more other 3D model editing techniques.

20. The method of claim 1, wherein the real target is at least one part of a person's body and/or at least one object.

21. The method of claim 20, wherein the real target is a person's head.

22. The method of claim 21, wherein the plurality of 3D feature groups includes one or more of the feature groups selected from the group comprising a jaw line feature group, a laryngeal prominence Feature group, an upper lip feature group, a lower lip feature group, a mouth feature group, a left ear feature group, a brow ridge feature group, a front hairline feature group, and a top head contour feature group.

23. A method of gesture-based editing of a 3D model of a real target comprising the following steps:
selecting and displaying on a display, a 2D projected view of a 3D default model, wherein the 3D default model comprises an overall set of vertices, wherein a plurality of subsets of the overall set of vertices forms a plurality of 3D feature groups, each one of which includes an ordered set of feature group points and is associated to a respective specific feature of the default model;

selecting a 2D image of a real target with a view which corresponds to the selected 2D projected view of the default model, and displaying the selected 2D image of the real target on the display;

acquiring at least one line traced by a user over the 2D image of the real target on the display that follows at least one real specific feature of the real target visible in the 2D image which correspond to at least one specific feature group;

identifying an ordered set of user points belonging to the at least one traced line;

matching the user points against the feature group points of the at least one specific feature group in a transformed 2D space of first transformed coordinate L and second transformed coordinate Th, where first transformed coordinate L of a point is a normalized length in a Cartesian coordinate system of the point in its ordered set of points joined by segments, and second transformed coordinate Th of the point is an angle of discrete vector difference in the Cartesian coordinate system between two discrete successive vectors respectively following and preceding the point in its ordered set, wherein a subset of user points is identified as a best match of the feature group points of the at least one specific feature group;

updating the default model into a 3D intermediate model by applying to the feature group points of the at least one specific feature group 3D geometric difference vectors calculated for each pair of feature group point and respective user point identified as best match of such feature group point; and smoothing the 3D intermediate model for obtaining a fitting model of the real target.

24. A system configured to execute a method of gesture-based editing of a 3D model of a real target comprising:

one or more processors configured to execute machine-readable instructions;

a memory for storing machine-readable instructions and data implementing the method of gesture-based editing of a 3D model of a real target; and an input/output interface connected to the one or more processors to allow a user to interact with the system, wherein the input/output interface includes a display;

wherein the one or more processors are connected to the memory to execute the machine-readable instructions, the instructions comprising the following steps:

selecting a 2D projected view of a 3D default model, the 3D model comprising an overall set of vertices, wherein a plurality of subsets of the overall set of vertices form a plurality of 3D feature groups, each 3D feature group comprising an ordered set of feature group points that are associated with a respective specific feature of the default model;

selecting a 2D image of a real target with a view which corresponds to the selected 2D projected view of the default model and displaying the selected 2D image of the real target on the display;

acquiring at least one line traced by a user over the 2D image of the real target on the display that follows at least one real specific feature of the real target visible in the 2D image which correspond to at least one specific feature group;

identifying an ordered set of user points belonging to the at least one traced line;

matching the user points against the feature group points of the at least one specific feature group in a transformed 2D space of first transformed coordinate L and second transformed coordinate Th, where the first transformed coordinate L of a point is a normalized length in a Cartesian coordinate system of the point in its ordered set of points joined by segments, and the second transformed coordinate Th of the point is an angle of discrete vector difference in the Cartesian coordinate system between two discrete successive vectors respectively following and preceding the point in its ordered set, wherein a subset of user points is identified as a best match of the feature group points of the at least one specific feature group; and updating the default model by applying to the feature group points of the at least one specific feature group 3D geometric difference vectors calculated for each pair of a feature group point and a respective user point identified as best match of such feature group point.

25. The system of claim 24, further comprising smoothing for obtaining a fitting model of the real target.

26. The system of claim 24, wherein the display is a touch-screen display.

27. The system of claim 24, wherein the input/output interface means further includes one or more of the following:

a keyboard, a pointing device, a port configured to acquire images, and one or more cameras connected to the processing means, wherein the processing means is configured to acquire at least one gesture of the user.

28. The system of claim 24, further comprising a robotic arm.

29. The system of claim 24, wherein the system is configured to plan hair transplantation procedures.

* * * * *